US007842722B2

(12) United States Patent
Lang

(10) Patent No.: US 7,842,722 B2
(45) Date of Patent: Nov. 30, 2010

(54) COMPOSITION AND METHODS FOR INHIBITING THE PROGRESSION MACULAR DEGENERATION AND PROMOTING HEALTHY VISION

(75) Inventor: John C. Lang, Cedar Hill, TX (US)

(73) Assignee: Alcon, Inc., Hunenberg (CH)

( * ) Notice: Subject to any disclaimer, the term of this patent is extended or adjusted under 35 U.S.C. 154(b) by 978 days.

(21) Appl. No.: 10/580,940

(22) PCT Filed: Dec. 14, 2004

(86) PCT No.: PCT/US2004/041813

§ 371 (c)(1),
(2), (4) Date: May 30, 2006

(87) PCT Pub. No.: WO2005/065669

PCT Pub. Date: Jul. 21, 2005

(65) Prior Publication Data

US 2007/0110826 A1    May 17, 2007

Related U.S. Application Data

(60) Provisional application No. 60/531,470, filed on Dec. 19, 2003.

(51) Int. Cl.
*A61K 31/355* (2006.01)
*A61K 31/07* (2006.01)
(52) U.S. Cl. .................... 514/458; 514/725; 514/912
(58) Field of Classification Search ............... 514/458, 514/725, 912
See application file for complete search history.

(56) References Cited

U.S. PATENT DOCUMENTS

| 3,998,753 | A | 12/1976 | Antoshkiw et al. |
| 4,254,100 | A | 3/1981 | Keller et al. |
| 4,657,928 | A | 4/1987 | Sorenson |
| 4,670,247 | A | 6/1987 | Scialpi |
| 6,582,721 | B1 | 6/2003 | Lang |
| 6,649,195 | B1 | 11/2003 | Gorsek |
| 2002/0182266 | A1 | 12/2002 | Bartels et al. |
| 2003/0064133 | A1 | 4/2003 | Blatt et al. |

FOREIGN PATENT DOCUMENTS

| DE | 101 09 798 A1 | 9/2002 |
| WO | WO 2005/065669 A1 | 7/2005 |

OTHER PUBLICATIONS

Areds Report No. 9, Age-Related Eye Disease Study Research Group: "A Randomized, Placebo-Controlled, Clinical Trial Of High-Dose Supplementation With Vitamins C And E And Beta Carotene For Age-Related Cateract and Vision Loss", Archives Of Ophthalmology, 119(10):1439-1452 (2001).
Beem, J Biol Chem 249:7298 (1974).
Berman, Biochemistry of the Eye, (Plenum Press, 1991), 309-330, 345-359 and 386-399.
Bernstein et al., Retinal Tubulin Binds Macular Carotenoids, Inv Ophthal & Vis Sci 38(1):167-175 (1997).
Bone and Landrum, Am Society for Nutritional Sciences J Nutr, 133:992-998 (2003).
Chandler et al., J. Biol. Chem 261:928-33 (1986).
Chaney, Textbook of Biochemistry With Clinical Correlations, John Wiley & Sons, 970-971 (1986).
Chatterjee and Ghosh, Arch, Ophthalmol 56:756-60 (1956).
Fischer, J Nutrition 113:462-469 (1983).
Hammond et al., Sex differences in macular pigment optical density: relation to plasma carotenoid concentrations and dietary patterns, Vision Research 36:2001-2012 (1996a).
Hammond et al., Cigarette smoking and retinal carotenoids: implications for age-related macular degeneration, Vision Research 36:3003-3009 (1996b).
Hammond et al., Dietary Modification of Human Macular Pigment Diensity, Inv Ophthal & Vis Sci 38 (9):1795-1801 (1997).
Handelman et al., Biological Control of Primate Macular Pigment: Biochemical and Densitometric Studies, Inv Ophthal & Vis Sci 32(2):257-267 (1991).
Harris, Nature 132:27-8 (1993).
Hooper et al., JAMA 244:1960-1961 (1980).
Jacques et al., Antioxidant Status in Persons With and Without Senile Cateract, Arch. Ophthalm. 106:337-340 (1988).
Karcioglu, Surv Ophthalmol 27:114-122 (1982).
Leure-Dupree, Retina 2:294-302 (1982a).
Leure-Dupree, Invest Ophthalmol Vis Sci 23:425-34 (1982b).
Machlin et al., Free Radical Tissue Damage: Protective Role of Antioxidant Nutrients, FASEB J 1:441-445 (1987).
Mansour et al., Effect of Antioxidant (Vitamin E) On The Progress of Cataracts In Emory Mice, ARVO Abstract #47, p. 138 (1984 Supplement).
Newsome, D.A., Oral Zinc in Macular Degeneration, Arch. Ophthalmol. 106:192-198 (1988).
Ohrloff and Hockwin, Graefe's Arch Clin Exp Ophthalmol 222:79-81 (1984).
Orten, Human Biochemistry 10th Edition, CV Mosby Co., p. 756-757 (1982).
PCT International Search Report of the related PCT Application No. PCT/US2004/041813, mailed Jun. 13, 2005.
Pennington, J Am Dietetic Assoc 86:876-91 (1986).
Purcell et al., Arch Ophthalmol 51:1-6 (1968).

(Continued)

*Primary Examiner*—Zohreh A Fay
(74) *Attorney, Agent, or Firm*—Teresa J. Schultz

(57) ABSTRACT

The present invention provides improved dietary supplements and methods for inhibiting the progression of macular degeneration and promoting healthy vision. The dietary supplements of the invention contain cobeadlets comprising vitamin E and carotenoids in the form of Vitamin A, lutein and/or zeaxanthing. The dietary supplements of the invention further contain Vitamin C, copper and zinc and may also contain such ingredients as rosemary, DHA, other vitamins and minerals.

2 Claims, No Drawings

OTHER PUBLICATIONS

Ringvold, Acta, Ophthalmologica 63:227-2 80 (1985).
Russell, Ann Int Med 99:227-239 (1983).
Seddon et al., Dietary Carotenoids, Vitamins A, C and E, and Advanced Age-Related Macular Degeneration, JAMA 272(8):1413-1420 (1994).
Snodderly, Evidence for protection against age-related macular degeneration by carotenoids and antioxidant vitamins, Am J Clin Nutr 62(suppl):1448S-1461S (1995).
Sparrow et al., 2001, Bioorganic & Medicinal Chemistry Letters, 11, 1533-1540.
Spector et al., Exp. Eye Res. 33:673-681 (1981).
Swanson, Biochem Biphy Res Comm 45:1488-1496 (1971).
Van Campen, J Nutrition 97:104-108 (1970).
Varma et al., Ophthalmic Res 9:421-431 (1977).
Varma et al., Ophthalmic Res 26:141-148 (1994).
Wagner, Geriatrics 40:111-125 (1985).
Williams, Pediat Res 1:823-826 (1977).

COMPOSITION AND METHODS FOR INHIBITING THE PROGRESSION MACULAR DEGENERATION AND PROMOTING HEALTHY VISION

This 371 application claims priority from PCT/US2004/041813 filed Dec. 14, 2004, and U.S. Provisional Patent Application Ser. No. 60/531,470 filed Dec. 19, 2003.

BACKGROUND OF THE INVENTION

1. Field of the Invention

The present invention generally relates to methods and compositions to alleviate eye diseases and, more specifically, to improved methods and compositions for the treatment of cataracts and macular degeneration.

2. Description of the Related Art

Macular degeneration associated with aging and drusen is an extremely significant concern, and is now a major cause of blindness in the United States for individuals over 65 years of age. Just at the period of time when the eyes are a most important sense, and is reading and watching television are often the most enjoyable avenues of entertainment, this disease robs the elderly patient of such possibilities.

The crystalline lens of the eye has only one disease state that we are aware of, and that is cataract. The lens loses its clarity as it becomes opacified, and vision is disturbed depending on the degree of opacification. There are different etiologies for cataracts such as a congenital lesion or trauma, which are well recognized. It is also known that some medicines such as cortisone-type preparations and glaucoma medications can cause cataracts, as can inborn metabolic errors such as galactosemia. These, however, are relatively uncommon in comparison to the common aging cataract, which shows an increase in frequency directly correlated with age.

The exact incidence of cataracts in the general population is difficult to determine because it depends on one's definition of a cataract. If defined as simply a lens opacity, then obviously the incidence is much higher than when defined as a lens opacity that significantly impacts vision. The pathogenesis of age-related cataracts and macular degeneration is incompletely understood.

The accumulation of drusen and lipofuscin and the loss of retinal pigment, hallmarks of macular degeneration, appear to be a consequence of the accumulation of biomolecular derivatives of those bioactive molecules involved in photoreception and signal processing, and normally detoxified, processed, and exported from the RPE (retinal pigment epithelium). While the importance of controlling the accumulation of lipofuscin and its dominant component $A_2E$, N-retinylidene-N-retinylethanolamine (Sparrow, 2001), which is responsible for converts visible-wavelength radiation into toxic ROSs (reactive oxygen species), no means for accomplishing this has been proposed and so the best means currently available for limiting the damage is by reducing the amount of radiation is available to the lipofuscin. There also is no effective treatment to date for the resulting biodegeneration, except laser photocoagulation in patients who develop abnormal vessels under the retina, i.e., subretinal neovascularization. The treatable group is a distinct minority of a much larger group. Individuals so afflicted can anticipate either a progressive deterioration or at times relatively static course, but no spontaneous improvement, since the basic architecture of the retina is destroyed. Occasionally, there may be variations in vision which seem to show improvement depending on such things as lighting in the room and potential resolution of fluid underneath the retina. The important point, however, is that when this sensitive neurological tissue is damaged, that damage is permanent.

In 1981, Spector et al. stated that there still remained questions concerning the mechanism and agents involved with massive oxidation of the lens tissue and its relationship to cataract development (Spector et al. 1981). They also noted that glutathione (GSH) can act as a reducing agent and free radical trapper. Glutathione peroxidase (GSHPx) and catalase are present to metabolize $H_2O_2$. While superoxide dismutase (SOD) can detoxify $O_2$, light can photochemically induce oxidation. However, Spector et al. believe that the actual roles of light and/or metabolically-generated oxidized components are unclear as to causing the observed oxidation products.

In 1987, Machlin et al. reported that there was some evidence that free radical damage contributed to the etiology of some diseases, including cataract (Machlin et al. 1987). They indicated that defenses against such free radical damage included Vitamin E, Vitamin C, beta carotene, zinc, iron, copper, manganese, and selenium.

In 1988, Jacques et al. reported that it is commonly believed that oxidative mechanisms are causally linked to, not simply associated with, cataract formation. According to Jacques et al. evidence suggests that GSHPx and SOD decrease with increasing degree of cataract.

Jacques et al. further reported that Vitamin E is believed to be a determinant of cataract formation and can act synergistically with GSHPx to prevent oxidative damage. They point out the possibility that Vitamin C may have a role in cataract formation and might influence GSHPx through its ability to regenerate Vitamin E.

Dietary supplements are taken for a variety of reasons including the improvement of vision or prophylaxis of vision loss. An example of a set of dietary supplements useful in promoting healthy eyes are the ICAPS® Dietary Supplements (Alcon Laboratories, Inc., Fort Worth, Tex.). Dietary supplements are generally in the form of powders, tablets, capsules or gel-caps and comprise a variety of vitamins, minerals, and herbal or other organic constituents. Some dietary supplements are formulated with beadlets.

Beadlets contain dietary substances and are generally small spheroids of less than about a millimeter in diameter. There are a variety of functions and purposes of beadlets. For example, beadlets may provide for the separate containment of ingredients within the dietary supplement to improve the stability of the entrapped ingredients.

Various beadlet compositions are known and can be obtained from a number of food ingredient or pharmaceutical manufacturers including H. Reisman Corp. (Orange, N.J.), BASF (Mount Olive, N.J.), BioDar (Israel), and Hoffmann-LaRoche (Nutley, N.J.). Particular beadlet compositions have been the subject of several patents including U.S. Pat. No. 4,254,100 (Keller et al.) and U.S. Pat. No. 3,998,753 (Antoshkiw et al.). Numerous methods of beadlet manufacture have been disclosed, e.g. in U.S. Pat. Nos. 4,670,247; 3,998,753 and published U.S. application No. 20030064133.

Current beadlet compositions used in dietary supplements generally are restricted to the use of inert ingredients and excipients complementary to a single nutritional compound. In other instances, when molecules of the same class are refined from a particular source, for example a major component with a minor related constituent, and both compounds produce parallel effects, such molecules may not necessarily be isolated but mixed together in a beadlet. These may be considered pseudo-single-component beadlets, and there are examples in the market place, e.g., Lutrinol® and FloraGLO® beadlets, which are a combination of lutein and zeaxanthin as formulated in Retoxil® Dietary Supplements. Examples of ingredients benefiting from beadlet confinement have included natural vitamins such as Vitamins A, D, E, and K; xanthophylls such as lutein, zeaxanthin, canthaxanthin, and astaxanthin; and carotenes, such as beta-carotene, lycopene, and retinol.

Recent data has suggested that the inclusion of xanthophylls and other carotenoids in dietary supplements may provide superior dietary supplements useful in enhancing the health of the eye. Studies have shown the selective uptake of the carotenoids, zeaxanthin and lutein, by the macula of the eye (Bernstein et al. 1997; Hammond et al. 1997; and Handelman et al. 1991). This earlier work revealed the presence of both lutein and its positional isomer, [R,R]-zeaxanthin. More recently, a second isomer of zeaxanthin has been found in the macula, the diastereomer meso-zeaxanthin, the [R,S] isomer of zeaxanthin (Bone & Landrum). These and related observations suggest both are essential for improved ocular health and protection of the macula.

Xanthophylls are effective phytochemical antioxidants and are known to localize in the macula of the retina. It has been suggested that the particular xanthophylls, zeaxanthin and its isomer lutein, may be beneficial in improving the health of the macula and the clarity of the lens. These molecules may function in a number of ways to protect the eye from high intensity radiation or other insults. It has been suggested that foveal proteins bind the xanthophylls, localize and concentrate xanthophylls within the fovea. Since xanthophylls are capable of absorbing photoexcitative radiation of short visible wavelength, they also may shield the light-sensitive, underlying cells of the neural retina and RPE. Such cells are responsible for high-definition vision and have been shown by epidemiological studies to be adversely affected by exposure to high intensity radiation or even chronic exposure to visible wavelength radiation. The carotenoids are believed to complement the activity of these cells, and also to protect them against photochemical insult. See, e.g., Snodderly (1995) and Seddon et al. (1994).

Studies also have shown that the portion of the retina associated with xanthophyll deposition undergoes one of the highest metabolic rates in the body (Berman 1991). The energy to sustain this metabolism is derived from oxidation. While the very lipophilic xanthophylls do not appear to undergo rapid turnover characteristic of water-soluble antioxidants (Hammond et al. 1997), continuous exchange of xanthophylls occurs in response to both environmental challenge and tissue environment, and their gradual depletion without nutritional replacement may portend tissue damage (Hammond et al. 1996a; Hammond et al. 1996b; and Seddon et al. 1994). The lack of rapid turnover also implicates the role of other synergistic antioxidants, vitamins C and E especially but also enzymatic antioxidants that are active in the redox cascade that passes the initial oxidative excitation to lower-energy and less damaging species.

The carotenes are conjugated $C_{40}$ compounds that include beta carotene (a provitamin A precursor). The carotenes are deeply colored compounds and are found throughout the plant kingdom, e.g., in leafy vegetables such as spinach and kale, and brilliantly colored fruits such as melons and pineapple. While the carotenes are ubiquitous in the plant kingdom, they generally are not available biosynthetically in mammals. Since the carotenes are essential for normal mammalian health, mammals need to ingest various sources of the carotenes, e.g., fruits and vegetables. The absence of carotenoids from the diet, especially the carotene derivative, vitamin A, is known to be associated with degenerative eye diseases.

SUMMARY OF THE INVENTION

The present invention is directed to improved cobeadlet formulations useful for inclusion in dietary supplements. In particular, the improved cobeadlets comprise one or more xanthophylls; one or more carotenes, retinoids or combinations thereof; one or more antioxidants; and excipients. Preferred cobeadlets may also contain one or more bioflavonoids. The cobeadlets are particularly useful for incorporation in dietary supplements customized for improving ocular nutrition. Their role includes stabilization of the highly oxidizable contents to chemical reaction or physical degradation, and their purpose is to provide concentrated more efficient carriers permitting the inclusion of a greater number of synergistic components in the supplement dosage form.

The present invention is also directed to improved dietary supplements comprising the improved cobeadlets. Preferred dietary supplements have been formulated as an aid to ocular health. The present invention is also directed to methods of using the cobeadlets and dietary supplements for improving nutritional health. The methods of the present invention are particularly directed to the enhancement of ocular health and the prophylaxis of retinal disorders, including age-related macular degeneration.

One advantage of the cobeadlets of the present invention is that they provide one or more xanthophylls and one or more carotenes in a single cobeadlet formulation. Because these molecules contain multiple, conjugated double bonds, they are highly susceptible to degradation. Consequently, antioxidants have been required in dietary supplements to prevent premature oxidation of xanthophylls and carotenes during processing, manufacture, and storage. By coupling these mutually vulnerable components and the necessary antioxidants in one cobeadlet, the amount of stabilizing (antioxidant) component in the overall dietary supplement can be reduced, since the stabilizing components are distributed more proximately to the xanthophylls and carotenes, thereby concurrently stabilizing both of these carotenoids. In addition, the carotenes and xanthophylls, together in a single cobeadlet, may serve to stabilize each other. Since the stabilizing antioxidant components are often in excess of the active xanthophyll and carotene component, the total amount of the stabilizing antioxidant and other excipients including osmolality modifiers and polymers can become important, especially in a dosage form in which the presence of excess excipient diminishes the amount of the nutritional components that can be contained in the dosage form. In other words, an excess of excipient may displace crucial amounts of other vitamins, minerals or other dietary substances in the dosage form.

Another advantage of the cobeadlets of the present invention is that the juxtaposition of the carotenes and xanthophylls in a single cobeadlet, with or without absorption enhancing excipients, may allow for absorption synergy and/or activity synergy, leading to enhanced nutritional efficacy of the dietary supplement. Such synergy may arise, for example, when their properties—physical, chemical or physiological—are sufficiently similar that the bioavailability or site-specific targeting of these active ingredients may be manipulated concurrently using the single cobeadlet technology. The synergy also arises from the utility of a more efficient beadleting process; fewer and lower levels of excipients permit the addition of either more or a greater variety of total active components in the entire dosage form.

A related advantage of the coupling of these and other nutritional components into one cobeadlet is the potential for manipulating and improving competitive absorption of these agents. For example, if the cobeadlets are also comprised of a timed-release polymer, the release of the nutritional components may be controlled and thus synchronized, e.g., delivering them to the upper intestine at the same time where solubilization by chylomicron-forming bile salts can facilitate synchronous absorption.

Another advantage of the cobeadlets is that, as a practical matter of formulation, the amounts of xanthophyll and carotene can be manipulated better as a single cobeadlet entity, as opposed to adjusting the individual xanthophyll and carotene components of the finished dietary supplement. In other words, the cobeadlet composition may be significantly altered while the dietary supplement preparation using the same size and number of cobeadlets (but now different cobeadlet composition) would be unaffected. For example, little or no change in dietary supplement preparation would be expected for a change in formulations in which a 3% lutein/ 0% zeaxanthin/3% weight/weight ("w/w") Vitamin A containing cobeadlet was replaced by a 0% lutein/3% zeaxanthin/3% w/w Vitamin A containing cobeadlet. And in both cases the amount of both the complementary antioxidant and other supplementary constituents within the cobeadlet may remain invariant. This simplifies the reformulation process of a complex dietary supplement (often containing 30 or more components) and would be useful in view of the need to respond to new scientific information directing modifications of nutritional components of dietary supplements. This advantage greatly improves the turn-around time and reduces the cost of reformulation of such dietary supplements.

Still another advantage of the cobeadlets of the present invention is that they allow better manipulation of the appearance of the dietary supplement. Because many carotenes and xanthophylls have multiple, conjugated double bonds, they are intensely colored (oranges to red) and hydrophobic. Thus, specialized techniques have been generally required to compress tablets containing such components so that the dietary supplement form does not crumble and the components do not "bleed" within the supplement form, and to coat the cobeadlet-containing supplement form uniformly and consistently so that no unattractive discoloration or pitting occurs. Combining the carotenes and xanthophylls in a single cobeadlet lessens the problems of tableting and tablet coating. Thus, once having developed a dietary supplement using a coating technology capable of screening and disguising imperfections introduced, by the cobeadlet onto the surface of the dosage form, minor reformulations of a single complex cobeadlet, would obviate the requirement to redevelop the entire dietary supplement coating and tableting technologies.

The application of the cobeadlet technology of the present invention to dietary supplements provides, and facilitates development of, enhanced nutritional supplementation. Such technology may aid in increasing bioavailability of the dietary substances and also provide ease in modifying compositions containing xanthophylls/carotenes and complementary antioxidants within the supplement. Such improvements are believed to be particularly useful in the enhancement of ocular nutrition and improved ocular health.

DETAILED DESCRIPTION PREFERRED EMBODIMENTS

According to the present invention, the elements of the composition are directed toward scavenging free radicals and oxidants or in other ways retarding disease progression of macular degeneration. The free radicals to which the present invention is directed primarily include superoxide. The oxidants primarily include peroxide.

As used herein, the term "dietary supplement" is meant to encompass any form of dietary supplement, such as the tablet, caplet, gelcap, etc.

The items and doses in the present invention are consistent with those readily available in health food stores. The composition is preferably in tablet or caplet form for oral administration, with the patient taking one to four tablets or caplets taken once or twice a day. The present invention, however, contemplates that the preferred total dosage can be administered as a single dose or other multiple part dosages. The composition may also be of the timed-release or delayed-release types. Further, for oral ministration, the present composition may be in capsules, lacquered tablets, or unlacquered tablets, according to well-known methods. In accordance with the preferred multiple dosages described above, each tablet or caplet is preferably composed approximately as follows:

Vitamin C

It has been known that there are high concentrations of Vitamin C both in the normal human lens and in the aqueous humor that surrounds the lens, and that this is an antioxidant (Harris 1933). It has also been shown in the past that generally increasing dietary Vitamin C generally increases the concentration of ascorbate in the aqueous humor and in the human lens (Ringvold 1985). It has also been known that Vitamin C concentrations decrease with age and, in particular, in patients who have senile cataract (Chatterjee 1956; Purcell 1968). However, the latter study concluded that a fall in the level of ascorbic acid is not related to the causation of cataract. Purcell concluded that the therapeutic administration of Vitamin C to patients with cataracts appears irrational.

There is no known optimal daily dose of Vitamin C, although the U.S. RDA is 60 mg. However, dosages of 2.0 grams and more have frequently been taken as a supplement for general health. Although ascorbic acid or rose hips can be used, the present composition preferably utilizes Vitamin C in the form of sodium ascorbate because of it being easily dissolved in the digestive system and causing relatively minimal irritation. The concentration is at about 200-250 mg/tablet or caplet, or a preferred total dosage of about 0.8-2 grams/day. In such concentrations, the Vitamin C represents about 20-30% by weight of each tablet or caplet, which includes active as well as inactive ingredients described below.

Vitamin E

Vitamin E is also a well-known antioxidant, as already mentioned (see also Mansour 1984). Vitamin E can work synergistically with Vitamin C in protecting vital cell function from endogenous oxidants (Orten 1982).

A very common Vitamin E supplementation consists of 400 International Units per day. While studies that used more than 800 IU per day have shown possible signs of toxicity, many common dietary supplements available in supermarkets have 1000 units of Vitamin E daily (e.g., Chaney 1986). The U.S. RDA is 30 IU. The present invention preferably uses Vitamin E in the form of d,l-alpha tocopherol acetate, for which 1 mg is equivalent to 1 IU. The preferred concentration is about 15 IU-400 IU per tablet or caplet or a total daily dosage of 30-800 IU of Vitamin E. This represents from about 1% to preferably less than 20% by weight of each tablet or caplet.

Zinc

Zinc is known to be important to the health of the retina and the function of Vitamin A (Russell 1983; Karcioglu 1982; Leure-duPree 1982). Zinc is a cofactor in an enzyme required for maintaining the bioavailability of folate (Chandler et al. 1986), and folate is important for healthy DNA and protein synthesis. Zinc is one supplement previously used in a study which showed it to be significantly better than placebo in retarding macular degeneration changes (Newsome 1988). Zinc is also known to be an important cofactor for a whole multitude of metalloenzymes, not the least of which is superoxide dismutase, which scavenges the potent oxidizer-superoxide. There are two types of SOD in mammalian cells. One type contains copper and zinc and is located in the cytosol and periplasmic space of the mitochondria. The other type contains manganese and is in the matrix of the mitochondria (see generally U.S. Pat. No. 4,657,928). Mitochondria are the site of the high metabolic activity, and rapid oxidative processes in the retina. These isoforms of SOD and zinc are also implicated in cataract because both superoxide dismutase activity and zinc are dramatically lower in cataract patients than in noncataract patients (Ohrloff 1984; Varma 1977; Swanson 1971). Zinc is also involved in enzymes related to the metabolism of vitamin A, regulating the levels of esterification. By so doing, zinc is implicated in regulating the hepatic storage, release, and transport of retinol, and thereby its bioavailability for ocular tissues (Russell 1983).

About 200 mg of zinc per day, although well-tolerated, has been shown to have is potential side effects, particularly blocking copper absorption, which results in the possibility of copper deficiency anemia (Fischer 1983). High doses also have been shown to have the effect of lowering high-density lipoprotein, which may exacerbate atherosclerosis (Hooper 1980).

The dosages of 100 mg zinc a day and 150 mg of zinc a day have been known in the past to be well tolerated without difficulty (Wagner 1985). The U.S. RDA is 15 mg. While other salt forms such as sulfate, picolinate, phosphate, and gluconate can be used, the present invention preferably provides the zinc in the form of zinc acetate, because of it being most readily dissolved, causing minimal irritation, and effecting most rapid, complete (highest amount), and greatest percentage conversion into plasma zinc content, all of which are most desirable aspects. The preferred daily dosage range is from the RDA to a maximum of about 100 mg of a bioavailable form of zinc, such as zinc acetate. This maximum amount of zinc in a less bioavailable form such as zinc oxide could range as high as 150 mg/day. Either form could be administered in either a tablet or caplet.

Copper

Copper is another important cofactor for metalloenzymes, and is a second necessary cofactor for superoxide dismutase (Beem 1974). Copper has been shown to decrease in individuals over 70 years of age and to be basically zero in cataractous lenses (Swanson 1971). If copper is significantly decreased, superoxide dismutase has been shown to have decreased function, thereby hampering an important protective lens mechanism (Williams 1977). Copper is also protective of zinc toxicity, which blocks some of the zinc absorption and, therefore, decreases bioavailability (Van Campen 1970).

Two to three mg of copper per day has been estimated to be safe and provide adequate daily dietary intake (Pennington 1986). Two mg is the U.S. RDA. Some copper absorption will be blocked by the 100 mg of daily zinc as provided above (Van Campen 1970). Therefore, the present composition preferably provides about 1-5 mg/day. This amount is considered safe because in the typical American diet, particularly among the elderly, zinc and copper are often significantly below minimum daily requirements. In this embodiment of the present invention, copper is provided preferably in the form of copper gluconate or an amino acid chelate and copper in such form typically represents less than about 3% by weight of each tablet or caplet for a typical BID administered supplement like ICaps® Lutein and Zeaxanthin Formula, and less than 1% for a typical QID administered supplement like ICaps® AREDS. Cupric oxide also has been utilized as a source of copper in supplements where the total available space in the dosage form is very limited, since the fraction of copper is higher in this compound.

Beta-Carotene

It is well-known that Vitamin A is essential for vision. Vitamin A, retinol, is a $C_{20}$ alkene, which is combined as retinal in the retina with opsin to form rhodopsin, a visual pigment. The transition of the cis form to the trans form of retinal results from excitation by light. Thus, clearly vitamin A is crucial in photoreception. Beta-carotene, a pro-vitamin A carotenoid, is a lipid-soluble orange pigment that can serve as a self-regulating source of retinal. Both deficiency and excess of retinol can lead to fetal abnormalities since vitamin A is associated with not only vision but also growth, reproduction, cell proliferation, cell differentiation, and proper immune function.

The amount of β-carotene converted to retinol is biologically controlled and dictated by the need for retinol. The control is exerted through the central symmetric is enzymatic cleavage of the $C_{40}$-carotenoid to the $C_{20}$-retinoid. Therefore, none of the types of vitamin A toxicity have been observed for β-carotene. Nonetheless, explicit β-carotene toxicity has been surprisingly unearthed. While treatment of a β-carotene deficiency reduced the incidence of esophageal and gastric cancers, a compromised handling of a xenobiotic was seen in connection with its use in treating lung cancer and cardiovascular disease in smokers given high daily doses (i.e., 30 mg/day) of β-carotene. As a consequence, smokers (a high risk category for AMD) are encouraged not to increase their supplemented level of β-carotene above the RDA level. This recommendation directly contradicts the recommendation coming from the 7-year ARED Study, in which about 17-24 mg were consumed (AREDS Research Group 2002).

The resolution of these conflicting recommendations, as prescribed below, is to provide a complete formulation, including the vitamins and minerals of a multivitamin consumed by two-thirds of those on the ARED study, maintaining the total carotenoids at the 15 mg, or lower, designated level. In this formulation, lutein and zeaxanthin are substituted for a portion of the β-carotene content, maintaining the daily dosage of β-carotene at the RDA, 3 mg per day. The amount per tablet will be based on the number of tablets recommended for the particular dosage form, generally two to four tablets per day.

Xanthophylls

While Xanthophylls are $C_{40}$ compounds, and are carotenoids, this subclass is distinguished by the presence of more polar groups. The lutein and zeaxanthin isomers have hydroxyl alcoholic groups on both ionone terminal rings, and this plays a profound role on the localization and use of these carotenoids. Binding proteins specific to these lipids, control their localization in the eye, both their total absolute amount and their relative amounts. For example, observations in both primates and humans (cadaver eyes, for example) have indicated that while lutein is the most abundant xanthophyll in the eyes, in the vicinity of the fovea the relative amount of zeaxanthin is greater than lutein. The xanthophylls all serve as antioxidants, quenchers of free radicals, and absorbers of blue light, and all of these are protective functions of these molecules for the underlying retina and its support tissue, the RPE. These xanthophylls are all isomers of one another; the zeaxanthins have one more of the double bonds in the conjugated sequence, and so lutein and zeaxanthin are positional isomers. And the two zeaxanthin isomers, 3,3'-[R,R] and 3,3'-[R,S] (the meso form) are diastereomers, differing at only one optical center. All three of these diols have been observed to be present in the macula.

Xanthophylls are typically considered to be very safe compounds, found in edible plants and vegetables, from melons to corn to spinach and kale. Epidemiology has shown the incidence of AMD is lower for those individuals consuming amounts in the higher quartiles and quintiles. GRAS status has been granted to lutein, in both the free alcohol and ester forms. Lutein appears interconvertible to the meso form of zeaxanthin, though the protein(s) responsible for the interconversion have not yet been identified and so the precise mechanisms and means of controlling them is unknown. As a consequence, some balance of these xanthophylls in both diet and supplementation appears most prudent.

Both epidemiologic and prospective clinical studies indicate that higher macular levels of xanthophylls protect the retina from oxidative stress. Some data supports an increased deficit in the middle-aged and elderly. Epidemiologic data discerned that levels above 6 mg/day of xanthophylls were beneficial in delaying onset of AMD. Studies of the is impact of diet on bioavailability suggest serum levels of xanthophylls increase within a period of about four to eight weeks, and macular pigment levels respond more slowly but generally within four to six months, probably dependent on age, sex, and other health and risk factors of the subject. These data also suggest that both the rate of increase and the plateau levels are dependent on the daily intake. The National Health and Nutrition Examination Survey (NHANES) levels, that is the normal intake, is about 2 mg/day. Thus, in the methods and compositions of the present invention, the total daily supplementation of xanthophylls is preferably in the range from 2 mg/day to 18 mg/day, more preferably less than about 16 mg/day.

The present invention is directed to improved cobeadlet formulations, improved dietary supplement formulations comprising the improved cobeadlets and methods of use. As used herein, "dietary supplement(s)" or the shortened form, "supplement(s)," refer to any finished, dietary supplement dosage form containing dietary substances and suitable for ingestion by a host, e.g., human or other mammal.

The cobeadlets of the present, invention comprise one or more xanthophylls; one, or more carotenes or retinoids or combinations thereof; one or more antioxidants; and one or more solidifying agents.

As used herein, "xanthophylls" refer to hydroxy- and keto-oxidized carotenes and their derivatives, including both free alcohols and esters; "carotenes" refer to any of the 40-carbon carotenes and their derivatives; "retinoids" refers to the 20-carbon Vitamin A (retinol) and its derivatives; and "carotenoids" refers to any of the xanthophylls, carotenes and retinoids or combinations thereof. Carotenoids may be synthetically derived or purified from natural sources. Synthetic preparations may contain different isomers of carotenoids than those contained in the natural preparations. Depending on intended use, natural, synthetic or mixtures of both types of carotenoids may be included in the cobeadlets of the present invention.

The xanthophyll component may be obtained from various sources such as vegetables and herbal components, such as corn, leafy green vegetables and marigolds; marine sources, such as krill; or microorganic sources, such as algae and gene-engineered bacterial or yeast sources. Xanthophylls may also be synthesized by methods known in the art and are available from various manufacturers. Examples of xanthophylls include, but are not limited to, lutein, zeaxanthin, astaxanthin, canthaxanthin, cryptoxanthin and related oleoresins (e.g., fatty acid mono and di-esters of xanthophylls). The xanthophyll purity and concentration in the various commercial sources will vary. For example, some sources may provide about a 1% weight/weight ("w/w") or less of xanthophyll in oil while other sources, e.g., Kemin Laboratories, Inc. (Des Moines, Iowa), may provide a source in excess of 20% w/w xanthophyll in oil. Xanthophyll sources may be preparations of individual xanthophylls or combinations thereof, and may range in concentration depending on the diluent, or in fact their absence since some preparations of powder or 'cake' may provide a more preferable raw material. For example, a xanthophyll preparation may comprise lutein as the sole xanthophyll or a combination of lutein and zeaxanthin, including combinations of the diastereomers of zeaxanthin ([R,R'], [R,S], [S,R], and [S,S]), wherein preferred combinations include a mixture of lutein, [R,R']-zeaxanthin and meso-zeaxanthin. Other preferred combination include a mixture of [R,R']-zeaxanthin and meso-zeaxanthin and/or a mixture of lutein and any one diastereomer of zeaxanthin. The inclusion of a combination of xanthophylls in the cobeadlets, and in particular ratios, may be particularly important when it is the intention to deliver such combinations to the host in ratios similar to those found in the retina broadly, or in the macula or fovea of the eye, specifically, or in other ratios which, when injested, support the ratios in the host tissues. Xanthophylls may also be included in the cobeadlets as conjugated derivatives, e.g., oleoresins of xanthophylls, as exemplified above.

The carotene, retinoid or combinations thereof component (hereinafter referred to as "carotene(s)/retinoid(s)") may be obtained from various sources such as vegetable and herbal sources, such as corn and leafy vegetables, and fermentation product sources available from the biotech industry. The carotenes/retinoids may also be synthesized by methods known in the art. Examples of carotenes include, but are not limited to, alpha-, beta-, gamma-, delta-, epsilon- and psi-carotene, isomers thereof. Examples or retinoids include, but are not limited to, Vitamin A and Vitamin A analogs (e.g., retinoic acid). The carotene/retinoid purity and concentration in the various commercial sources will vary. For example, some sources may provide about a 1% w/w or less of carotene/retinoid in oil, or as an oil suspension, or in a protected dry form, e.g., a cobeadlet.

The concentrations of the xanthophylls and carotenes/retinoids in the cobeadlets will vary, but will be in amounts useful for inclusion of the cobeadlets in dietary supplements. In general, the combined concentration of xanthophylls and carotenes/retinoids in the cobeadlets will be in the range of about 0.1 to 10% w/w. Preferred carotenoid concentrations, which are generally dependent on the selection of particular carotenes/retinoids and xanthophylls and their relative ratios, will be about 0.5 to 7% w/w. The individual concentrations of the xanthophylls and the carotenes/retinoids will not necessarily be the same. Preferred cobeadlets will have a concentration ratio from about 1:10 to about 10:1 of xanthophylls:carotenes/retinoids and the most preferred cobeadlets will have concentration ratios from about 2:1 to about 1:2 of xanthophylls:carotenes/retinoids.

The most preferred cobeadlets of the present invention will comprise 0.5 to 7% w/w of lutein/zeaxanthin (xanthophylls) and 0.5 to 7% w/w of β-carotene (carotenes/retinoids).

As stated above, the cobeadlets will also contain one or more antioxidants. The antioxidants can be hydrophobic or hydrophilic. The antioxidants serve to inhibit the oxidative, photochemical and/or thermal degradation of the carotenoid components. Since antioxidants are also thought to be useful in nutritional health, they may also provide some nutritional benefit to the host. In general, the antioxidants will be natural antioxidants or agents derived therefrom. Examples of natural antioxidants and related derivatives include, but are not limited to, vitamin E and related derivatives, such as tocotrienols, alpha-, beta-, gamma-, delta- and epsilon-tocopherol, and their derivatives, such as the corresponding acetates, succinates; Vitamin C and related derivatives, e.g., ascorbyl palmitate; and natural oils, such as oil of rosemary. Preferred cobeadlets will contain one or more hydrophobic antioxidants. The amount of antioxidant(s) contained in the cobeadlet will be an amount effective to inhibit or reduce the oxidative, photochemical and/or thermal degradation of the carotenoid components. Such an amount is referred to herein as "an effective amount of one or more antioxidants." In general, such an amount will range from about 0.1 to 10 times the amount of the xanthophyll and carotene/retinoid components and any other chemically sensitive components present, e.g., bioflavonoids. Preferred cobeadlets, which will generally comprise about 0.5-25% w/w of carotenoids alone, or including bioflavonoids, will contain about 2 to 10% w/w of antioxidant. The most preferred cobeadlets will contain Vitamin E and, optionally, ascorbyl palmitate.

The cobeadlets will also comprise one or more solidifying, bulking and agglomerating agents (collectively referred to herein as "solidifying agent(s)"). The solidifying agent(s) aid in transforming the carotenoid and antioxidant components into a solid suitable for granulation, tableting or blending prior to encapsulation, of the cobeadlet in the dietary supplement. The solidifying agents are particularly useful when the carotenoid/antioxidant components are in oils or oil suspensions. Examples of solidifying agents useful in the preparation of the cobeadlets include, but are not limited to, sucrose, glucose, fructose, starches (e.g., corn starch), syrups (e.g., corn syrup), and ionic and nonionic polymers including, but not limited to, PEGs and other poly ether-like alkoxy cellulosics (HPMC), gellan, carrageenans, Eucheuma gelatenae, hyaluronates, alginates, chondroitin sulfate, pectins, and proteins, (e.g., collagen or their hydrolyzed products (e.g., gelatins or polypeptides)). Other solidifying agents known to those skilled in the art of cobeadlet and dietary supplement preparation may also be used in the preparation of the cobeadlets of the present invention. The amount of solidifying agent(s) will vary, depending on the other components contained in the cobeadlet, but will generally comprise the majority weight and volume of the cobeadlet.

Optionally, the cobeadlets of the present invention may also contain one or more bioflavonoids and/or glycosidic bioflavonoids. Bioflavonoids, or "flavonoids," are flavone- and isoflavone-like structures found primarily in fruits and vegetables. Bioflavonoids are commercially available or may be synthesized by methods known in the art. Examples of bioflavonoids include, but are not limited to, quercetin, acacetin, liquritin, rutin, taxifulin, nobiletin, tangeretin, apigenin, chyrsin and kaempferol, and their derivatives, such as the corresponding methoxy-substituted analogs. The bioflavonoids may be useful in nutritional health as modulators of the rates of in vivo enzyme-mediated reactions. The bioflavonoids may also provide antioxidant activity and may be included in the cobeadlet for this purpose.

Other oils may be present in the cobeadlets of the present invention. The cobeadlets will typically comprise an amount of vegetable oils or oleoresins, since the separate carotene/retinoid and/or xanthophyll components to be added to the cobeadlets are generally commercially available as a diluted vegetable oil or oil suspension, or as an oleoresin extract. Such an amount of oil/oleoresin typically ranges from about 1 to 100 times the xanthophyll or carotene content in the cobeadlet. For example, a xanthophyll extract to be included in a cobeadlet may contain 20% w/w lutein, 2% w/w zeaxanthin and 78% vegetable oil/oleoresin. Other oils may also be included in the cobeadlets.

The cobeadlets of the present invention may also comprise additional excipients useful in preparing and finishing the cobeadlets. Such excipients may include timed-release polymer coating agents useful in prolonging dissolution of the cobeadlet in the digestive tract. Examples of such polymers include, but are not limited to ionic and nonionic polymers, such as PEGs and other poly ether-like alkoxy cellulosics (HPMC), gellan, carrageenans, Eucheuma gelatenae, starch, hyaluronates, chondroitin sulfate, pectins, and proteins, e.g., collagen. Since the xanthophyll/carotenes are highly pigmented, coating technology may be applied to the cobeadlet in order to provide a cobeadlet of uniform color. Examples of color coating agents may include, but are not limited to, polymers, colorants, sealants and surface active agents including, not limited to, fatty acids and esters, di- and triglycerides, phospholipids including mono- and di-alkyl is glyceryl phosphates, nonionic agents (sugars, polysaccharides, e.g., HPMC and polysorbate 80) and ionic agents.

The above-described ingredients contained in the cobeadlets may, in some cases, form microspheres within the cobeadlet. The cobeadlets may be of various size and shape.

In general, however, the cobeadlets will be spheroid with an approximate diameter of about 0.2 microns to 800 microns.

The cobeadlets may be manufactured using a number of techniques known in the art. For example, the cobeadlets may be prepared by blending and granulation of the ingredients, followed by drying. The details of these processes may vary according to the sequence of addition, duration and conditions for granulation, and techniques employed for drying. Preferred methods will include a low-temperature, low light-exposure drying step capable of maintaining stability of the cobeadlet. An inert, or reduced-oxygen, atmosphere may also be employed in the manufacture of the cobeadlets in order to further reduce degradation of sensitive components.

The present invention further provides dietary supplements containing the cobeadlets of the invention. The cobeadlets described herein are preferably present in the dietary supplements of the invention in an amount sufficient to provide the daily dosage (amount consumed per day) when the recommended number of dietary supplements is ingested per day. Furthermore, the dietary supplements of the invention may contain a mixture of different cobeadlets, each different cobeadlet containing multiple, but different, components described herein. That is, a portion of the cobeadlets contained in a dietary supplement as described herein may contain β-carotene, lutein and zeaxanthin, while another portion of the cobeadlets contained in the dietary supplement contains Vitamin C, Vitamin E, copper and zinc. It is contemplated that any combination of components may be present in a particular cobeadlet of the invention. It is critical, however, that the dietary supplement as described herein contain the described amounts of at least Vitamin C, Vitamin E, lutein, zeaxanthin, copper and zinc. β-carotene will also be present in preferred dietary supplements of the invention. Each preferred component will typically be contained within a cobeadlet with at least one other component.

The following Examples, Examples 1 and 2, illustrate preferred cobeadlets of the present invention. Example 1 illustrates the use of a conventional type of beadlet formulation and Example 2 illustrates a more recent type of beadlet in which any biohazard related to an animal-sourced matrix component has been removed. The amount of water present in the following cobeadlet examples may vary due to process and storage conditions but will generally range from about 1-10% w/w; as such, the other component percentage amounts may fluctuate slightly, but will be in the same relative proportion with respect to each other.

EXAMPLE 1

| Ingredient | Amount % |
| --- | --- |
| Carotenoid oleoresin | 30% |
| Hydrolyzed gelatin | 33% |
| Sucrose | 13% |
| Ascorbyl palmitate | 2% |
| Tocopherols | 1% |
| Rosemary | 1% |
| Corn starch | 15% |
| Water | 5% |

EXAMPLE 2

| Ingredient | Amount % |
| --- | --- |
| Carotenoid oleoresin | 20% |
| Sodium alginate | 32% |
| Isolated soy protein | 15% |
| Hydroxypropyl cellulose | 10% |
| Ethoxylated glycerides | 6% |
| Rosemary or other antioxidant | 5% |
| Sucrose ester | 6% |
| Ca as the chloride salt | 5% |
| Water | 1% |

The following sets of examples, Examples 2 and 3, are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The composition in Example 3 describes meaningful formulations for individuals who are AMD patients. These compositions and dosing regimens would be appropriate and sufficient for the daily supplement requirement of such patients.

EXAMPLE 3A

| Ingredient | Amount (per tab) @ QID |
| --- | --- |
| Beta Carotene | 0.75 mg |
| Lutein | 2 mg |
| Zeaxanthin | 1 mg |
| Vitamin C | 125 mg |
| Vitamin E | 100 IU |
| Copper | 0.4 mg |
| Zinc | 20 mg |
| Vitamin D | 100 IU |
| Vitamin K | 6.25 |
| Vitamin B1 (thiamin) | 0.375 mg |
| Vitamin B2 (riboflavin) | 2.5 mg |
| Vitamin B3 (niacin) | 5 mg |
| Vitamin B6 | 0.5 mg |
| Folate/Folic Acid | 100 μg |
| Vitamin B-12 | 1.5 μg |
| Biotin | 7.5 μg |
| Pantothenic Acid | 2.5 mg |
| Phosphorus | 27.25 mg |
| Iodine | 37.5 mg |
| Magnesium | 25 mg |
| Selenium | 17.5 μg |
| Manganese | 0.5 mg |
| Chromium | 0.030 mg |
| Molybdenum | 18.75 μg |
| Potassium | 20 mg |
| Lycopene | 0.075 mg |
| DHA | <25 mg |
| Rosemary | >2 mg |
| Water | 5 |

The following example, Example 3B, indicates that observations may recommend a combination of different isomers of zeaxanthin, not just all of one or the other. Alternatively in Example 3A the inference would be correctly drawn to interpret the "zeaxanthin" to represent a ratio of zeaxanthins, from 0 to infinite, that is all of one or the other. The same inference would be accurate for the Examples in the other sets.

EXAMPLE 3B

| Ingredient | Amount (per tab) @ QID |
| --- | --- |
| Beta Carotene | 0.75 mg |
| Lutein | 2 mg |
| [R,R]-Zeaxanthin | 0.5 mg |
| [R,S]-Zeaxanthin | 0.5 mg |
| Vitamin C | 125 mg |
| Vitamin E | 100 IU |
| Copper | 0.4 mg |
| Zinc | 20 mg |

-continued

| Ingredient | Amount (per tab) @ QID |
|---|---|
| Vitamin D | 100 IU |
| Vitamin K | 6.25 μg |
| Vitamin B1 (thiamin) | 0.5 mg |
| Vitamin B2 (riboflavin) | 2.5 mg |
| Vitamin B3 (niacin) | 5 mg |
| Vitamin B6 | 0.5 mg |
| Folate/Folic Acid | 100 μg |
| Vitamin B-12 | 1.5 μg |
| Biotin | 7.5 μg |
| Pantothenic Acid | 2.5 mg |
| Phosphorus | 25 mg |
| Iodine | 37.5 mg |
| Magnesium | 25 mg |
| Selenium | 10 μg |
| Manganese | 0.5 mg |
| Chromium | 0.030 mg |
| Molybdenum | 18.75 μg |
| Potassium | 20 mg |
| Lycopene | 0.075 mg |
| DHA | <25 mg |
| Rosemary | >2 mg |
| Water | 5 |

The following example, Example 3C, provides higher concentrations of carotenoids for individuals with low serum or pigment levels.

EXAMPLE 3C

| Ingredient | Amount (per tab) @ QID |
|---|---|
| Beta Carotene | 0.75 mg |
| Lutein | 11.25 mg |
| Zeaxanthin | 3.75 mg |
| Vitamin C | 125 mg |
| Vitamin E | 100 IU |
| Copper | 0.4 mg |
| Zinc | 20 mg |
| Vitamin D | 100 IU |
| Vitamin K | 6.25 μg |
| Vitamin B1 (thiamin) | 0.5 mg |
| Vitamin B2 (riboflavin) | 2.5 mg |
| Vitamin B3 (niacin) | 5 mg |
| Vitamin B6 | 0.5 mg |
| Folate/Folic Acid | 100 μg |
| Vitamin B-12 | 1.5 μg |
| Biotin | 7.5 μg |
| Pantothenic Acid | 2.5 mg |
| Phosphorus | 25 mg |
| Iodine | 37.5 mg |
| Magnesium | 25 mg |
| Selenium | 10 μg |
| Manganese | 0.5 mg |
| Chromium | 0.030 mg |
| Molybdenum | 18.75 μg |
| Potassium | 20 mg |
| Lycopene | 0.075 mg |
| DHA | <25 mg |
| Rosemary | >2 mg |
| Water | 5 |

The compositions in Examples 4 describe meaningful formulations for individuals interested in maintaining ocular health. The composition and dosing regimen of Example 4A would be appropriate and sufficient for the daily supplement requirement of such patients.

EXAMPLE 4A

| Ingredient | Amount (per tab) @ BID |
|---|---|
| Beta Carotene | 1.5 mg |
| Lutein | 2 mg |
| Zeaxanthin | 1 mg |
| Vitamin C | 200 mg |
| Vitamin E | 75 IU |
| Copper | 0.5 mg |
| Zinc | 20 mg |
| Vitamin D | 200 IU |
| Vitamin K | 12.5 μg |
| Vitamin B1 (thiamin) | 0.751 mg |
| Vitamin B2 (riboflavin) | 5.0 mg |
| Vitamin B3 (niacin) | 10 mg |
| Vitamin B6 | 1 mg |
| Folate/Folic Acid | 200 μg |
| Vitamin B-12 | 3.0 μg |
| Biotin | 15 μg |
| Pantothenic Acid | 5 mg |
| Phosphorus | 54.5 mg |
| Iodine | 75 mg |
| Magnesium | 50 mg |
| Selenium | 35 μg |
| Manganese | 1 mg |
| Chromium | 0.060 mg |
| Molybdenum | 37.5 μg |
| Potassium | 40 mg |
| Lycopene | 0.150 mg |
| DHA | <50 mg |
| Rosemary | >2 mg |
| Water | TBD |

The compositions in Examples 4B describe meaningful formulations for individuals interested in maintaining ocular health yet who have a need for higher levels of carotenoids because either their serum or pigment levels are low. The composition and dosing regimen of Example 4B would be appropriate and sufficient for the daily supplement requirement of such patients.

EXAMPLE 4B

| Ingredient | Amount (per tab) @ BID |
|---|---|
| Beta Carotene | 1.5 mg |
| Lutein | 3 mg |
| Zeaxanthin | 1.5 mg |
| Vitamin C | 200 mg |
| Vitamin E | 100 IU |
| Copper | 0.5 mg |
| Zinc | 20 mg |
| Vitamin D | 200 IU |
| Vitamin K | 12.5 μg |
| Vitamin B1 (thiamin) | 0.751 mg |
| Vitamin B2 (riboflavin) | 5.0 mg |
| Vitamin B3 (niacin) | 10 mg |
| Vitamin B6 | 1 mg |
| Folate/Folic Acid | 200 μg |
| Vitamin B-12 | 3.0 μg |
| Biotin | 15 μg |
| Pantothenic Acid | 5 mg |
| Phosphorus | 54.5 mg |
| Iodine | 75 mg |
| Magnesium | 50 mg |
| Selenium | 35 μg |

-continued

| Ingredient | Amount (per tab) @ BID |
|---|---|
| Manganese | 1 mg |
| Chromium | 0.060 mg |
| Molybdenum | 37.5 µg |
| Potassium | 40 mg |
| Lycopene | 0.150 mg |
| DHA | <50 mg |
| Rosemary | >2 mg |
| Water | TBD |

The compositions in Example 4C describe meaningful formulations for individuals interested in maintaining ocular health, yet whose diet does not require the supplementation with a multivitamin. The composition and dosing regimen of Example 4C would be appropriate and sufficient for the daily supplement requirement of such patients.

EXAMPLE 4C

| Ingredient | Amount (per tab) @ BID |
|---|---|
| Beta Carotene | 1.5 mg |
| Lutein | 2 mg |
| Zeaxanthin | 1 mg |
| Vitamin C | 200 mg |
| Vitamin E | 75 IU |
| Copper | 0.5 mg |
| Zinc | 20 mg |
| Vitamin B2 (riboflavin) | 5.0 mg |
| Folate/Folic Acid | 100 µg |
| Vitamin B-12 | 3.0 µg |
| Selenium | 20 µg |
| Manganese | 5.0 mg |
| Lycopene | 0.075 mg |
| DHA | 12.5 mg |
| Rosemary | >2 mg |
| Water | TBD |

The composition in Example 4D describes a meaningful formulation for individuals interested in maintaining ocular health, but have a greater need for the xanthophylls. This composition and dosing regimen would be appropriate and sufficient for the daily supplement requirement of such patients.

EXAMPLE 4D

| Ingredient | Amount (per tab) @ BID |
|---|---|
| Beta Carotene | 1.5 mg |
| Lutein | <4 mg |
| Zeaxanthin | <2 mg |
| Vitamin C | <200 mg |
| Vitamin E | <200 IU |
| Copper | 0.5 mg |
| Zinc | 20 mg |
| Vitamin B2 (riboflavin) | 5.0 mg |
| Folate/Folic Acid | 100 µg |
| Vitamin B-12 | 3.0 µg |
| Selenium | 20 µg |
| Manganese | 5.0 mg |
| Lycopene | 0.075 mg |
| DHA | 12.5 mg |
| Rosemary | >2 mg |
| Water | TBD |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

United States Patents and Published Applications
U.S. Pat. No. 3,998,753
U.S. Pat. No. 4,254,100
U.S. Pat. No. 4,657,928
U.S. Pat. No. 4,670,247
20030064133
Books
Berman, BIOCHEMISTRY OF THE EYE, (Plenum, 1991).
Chaney TEXTBOOK OF BIOCHEMISTRY WITH CLINICAL CORRELATIONS, John Wiley & Sons, pp. 970-1 (1986)
Other Publications
Beem J BIOL CHEM 249:7298 (1974)
Bernstein et al., *Retinal Tubulin Binds Macular Carotenoids*, INV OPHTHAL & VIS SCI 38(1):167-175 (1997).
Bone and Landrum,
Chandler et al., J. BIOL. CHEM 261:928-33 (1986)
Chatterjee ARCH, OPHTHALMOL 56:756-60 (1956)
Fischer J NUTRITION 113:462-9 (1983)
Hammond et al., *Sex differences in macular pigment optical density: relation to plasma carotenoid concentrations and dietary patterns*, VISION RESEARCH 36:2001-2012 (1996a).
Hammond et al., *Cigarette smoking and retinal carotenoids: implications for age-related macular degeneration*, VISION RESEARCH 36:3003-3009 (1996b).
Hammond et al., *Dietary Modification of Human Macular Pigment Density*, INV OPHTHAL & VIS SCI 38(9):1795-1801 (1997).
Handelman et al., *Biological Control of Primate Macular Pigment: Biochemical and Densitometric Studies*, INV OPHTHAL & VIS SCI 32(2):257-267 (1991).
Harris, NATURE 132:27-8 (1993)
Hooper JAMA 244:1960-1 (1980)
Jacques et al., *Antioxidant Status in Persons With and Without Senile Cataract*, ARCH. OPHTHALM. 106:337 (1988).
Karcioglu SURV OPHTHALMOL 27:114-22 (1982)
Leure-duPree RETINA 2:294-302 (1982a)
Leure-duPree INVEST OPHTHALMOL VIS SCI 23:425-34 (1982b)
Machlin et al., *Free Radical Tissue Damage: Protective Role of Antioxidant Nutrients*, FASEB J 1:441-445 (1987).
Newsome, D. A., *Oral Zinc in Macular Degeneration*, ARCH. OPHTHALMOL. 106:192-198 (1988).
Ohrloff GRAEFE's ARCH CLIN EXP OPHTHALMOL 222:79-81 (1984)

Orten HUMAN BIOCHEMISTRY 10th Edition, CV Mosby Co., p. 756 (1982)
Pennington J AM DIETETIC ASSOC 86:876-91 (1986)
Purcell ARCH, OPHTHALMOL 51:1-6 (1968)
Ringvold ACTA, OPHTHALMOLOGICA 63:227-80 (1985)
Russell ANN INT MED 99:227-39 (1983)
Seddon et al., *Dietary Carotenoids, Vitamins A, C and E, and Advanced Age-Related Macular Degeneration*, JAMA 272 (8): 1413-1420 (1994).
Snodderly, *Evidence for protection against age-related macular degeneration by carotenoids and antioxidant vitamins* AM J CLIN NUTR 62 (suppl):1448S-1461S (1995).
Spector et al., EXP. EYE RES. 33:673 (1981).
Swanson BIOCHEM BIPHY RES COMM 45:1488-96 (1971)
Van Campen J NUTRITION 97:104-8 (1970)
Varma OPHTHALMIC RES 9:421-31 (1977)
Wagner GERIATRICS 40:111-25 (1985)
Williams PEDIAT RES 1:823 (1977)

I claim:

1. A dietary supplement for maintaining ocular health, said supplement comprising cobeadlets, wherein the cobeadlets comprise 30% w/w carotenoid oleoresin, 1% w/w tocopherols, and 1% w/w rosemary and wherein the dietary supplement comprises:
   a total amount of β-carotene of 0.75 mg;
   a total amount of lutein of 2 mg;
   a total amount of zeaxanthin of 1 mg;
   a total amount of vitamin C of 125 mg;
   a total amount of vitamin E of 100 IU;
   a total amount of copper of 0.4 mg;
   a total amount of zinc of 20 mg;
   a total amount of vitamin D of 100 IU;
   a total amount of vitamin K of 6.25 mg;
   a total amount of vitamin B1 of 0.375 mg;
   a total amount of vitamin B2 of 2.5 mg;
   a total amount of vitamin B3 of 5 mg;
   a total amount of vitamin B6 of 0.5 mg;
   a total amount of folate/folic acid of 100 μg;
   a total amount of vitamin B-12 of 1.5 μg;
   a total amount of biotin of 7.5 μg;
   a total amount of pantothenic acid of 2.25 mg;
   a total amount of phosphorus of 27.25 mg;
   a total amount of iodine of 37.5 mg;
   a total amount of magnesium of 25 mg;
   a total amount of selenium of 17.5 μg;
   a total amount of manganese of 0.5 mg;
   a total amount of chromium of 0.030 mg;
   a total amount of molybdenum of 18.75 μg;
   a total amount of potassium of 20 mg;
   a total amount of lycopene of 0.075 mg
   a total amount of DHA of <25 mg; and
   a total amount of rosemary of >2 mg.

2. The dietary supplement of claim 1, wherein dietary supplement comprises about 1.0% to 25% by weight cobeadlets.

* * * * *